United States Patent [19]

Brendel et al.

[11] Patent Number: 4,801,299
[45] Date of Patent: Jan. 31, 1989

[54] BODY IMPLANTS OF EXTRACELLULAR MATRIX AND MEANS AND METHODS OF MAKING AND USING SUCH IMPLANTS

[75] Inventors: Klaus Brendel; Raymond C. Duhamel, both of Tucson, Ariz.

[73] Assignee: University Patents, Inc., Westport, Conn.

[21] Appl. No.: 582,504

[22] Filed: Feb. 22, 1984

Related U.S. Application Data

[63] Continuation-in-part of Ser. No. 503,203, Jun. 10, 1983.

[51] Int. Cl.⁴ .................... A01N 1/02; A61L 17/00
[52] U.S. Cl. ........................................ 623/1; 623/7; 623/16; 623/66; 435/1; 128/DIG. 8; 8/94.11; 8/94.15; 8/94.17; 8/94.18
[58] Field of Search ............... 3/1, 1.4, 1.9; 8/94.11, 8/94.15, 94.17, 94.18; 128/DIG. 8; 424/DIG. 13; 435/1; 623/1, 7, 16, 66

[56] References Cited

U.S. PATENT DOCUMENTS

| | | | |
|---|---|---|---|
| 3,649,163 | 3/1972 | McCosker | 8/99.11 |
| 4,323,358 | 4/1982 | Lentz et al. | 8/94.11 |
| 4,352,887 | 10/1982 | Reid et al. | 435/240 |
| 4,383,832 | 5/1983 | Fraefel et al. | 8/94.33 |

OTHER PUBLICATIONS

Brendel, K. and Meezan, E., "Vascular Basement Membranes: Preparation and Properties of Material Isolated With the Use of Detergents." *In the Cetebral Microvasculature: Investigation of the Blood-Brain Barrier* (Eisenberg, H. M. and Suddith, R. L., eds.) Advances in Experimental Medicine and Biology, vol. 131, pp. 89–103, Plenum Publishing Co., New York (1980).

Carlson, E. C., Brendel, K., Hjelle, J. T. and Meezan E., "Ultrastructural and Biochemical Analysis of Isolated Basement Membranes from Kidney Glomeruli ruli and Tubules, and Brain and Retinal Microvessels." J. Ultrastruct. Res. 62: 26–53 (1978).

Duhamel, R. C., Meezan, E. and Brendel, K., "Morphology of Bovine Cerebral and Retinal Microvascular Basement Membranes and Electrophoretic Characterization of Differential Extracts." *In Recent Advances in Microcirculatory Research* (Gaehtgens, P., ed.) S. Karger, Basel, Bibl. Anat. 20: 134–137 (1980).

Meezan. E., Brendel. K., Hjelle, J. T. and Carlson, E. C. "A Versatile Method for the Isolation of Ultrastructurally and Chemically Pure Basement Membranes without Sonication." In Biology and Chemistry of Basement Membranes (Kefalides, N. A., ed.) pp. 17–30, Academic Press, New York (1978).

Meezan, E., Nagle, R. B., Johnson, P., Wagner, C., White R. and Brendel, K. "Structural and Functional Properties of Acellular, Bistoarchitecturally Intact Basement Membranes."]In *Frontiers of Matrix Biology*, vol. 7, Biochemistry and Pathology of Basement Membranes. (Robert, A., Boniface, R. and Robert, L. eds.) pp. 101–119, S. Karger, Basel (1979).

Meezan, E., Hjelle, J. T., Brendel, K. and Carlson, E. C. "A Simple, Versatile Non–Disruptive Method for the Isolation of Morphologically and Chemically Pure Basement Membranes from Several Tissues." Life Sci. 17: 1721–1732 (1975).

Brendel, K., Meezan, E. and Nagle, R. B. "The Acellular Perfused Kidney: A Model for Basement Membranes Permeability," In *Biology and Chemistry of Basement Membranes* (Kefalides, N. A., ed) pp. 177–193, Academic Press, New York (1978).

Kuttan, R., Spall, R. D. Duhamel, R. C., Sipes, I. G. Meezan, E. and Brendal, K. "Preparation and Composition of Alveolar Extra–Cellular Matrix and Incorporated Basement Membrane," Lung 159:333–345 (1981).

Duhamel, R. C., Meezan, E. and Brendel, K. "Selective Solubilization of Two Populations of Polypeptides from Bovine Retinal Basement Membranes," Exp. Eye Res. 36: 257–268 (1983).

Lafranconi, M., Spall, R., Sipes, G., Duhamel, R. C., Meezan, E. and Brendel, K. "Rapid Isolation of Type II Pneumocytes with Magnetic Removal of Macrophages", Experimental Lung Research 4:191–204 (1983). Elsevier Science Publishing Co., Inc. 1983.

Ohno, M., Ngle, R. B., Meezan, E. and Brendel, K., "Isolation and Characterization of Human Placental Chorionic Villar Extracellular Matrix"]Journal of Supramolecular Structure 12:457–466 (1979) Alan R. Liss, Inc. 1979.

Ohno, M., Meezan E., and Brendel K. "Human Placental Chorionic Villar Extracellular Matrix 2. Solubilization and Characterization from Villar Fragments Fractionated According to Their Size", Biological Research in Pregnancy, vol. 1 No. 2–1980 (pp. 79–80). t Ohno, M., Spall, R., Nagle, R. B., Brendel K., and Meezan, E. "Human Placental Chorionic Villar Extracellular Matrix 1, Preparation and Chemical Composition from Villar Fragments Fractionated According to Their Size." International Journal of Biological Research in Pregnancy, vol. 1, No. 1 (pp. 38–47).

Johnson, P. C. Duhamel, R. C. Meezan, E. and Brendel, K. "Preparation of Cell–Free Extracellular Matrix from Human Peripheral Nerve", Muscle and Nerve, 5:335–344 (1982), John Wiley & Sons, INc. 1982.

Spall, R., Sundheimer, D., Nagle, R., and Brendel, K. "Rate Hepatocytes in Suspension Culture and on Basement Substrate" (Paper 1978).

*Primary Examiner*—Kriellion Morgan
*Attorney, Agent, or Firm*—Barbara A. Shimei; Stanley Sacks

[57] ABSTRACT

A sterile body implant is derived from a body structure having as its major protein component collagens in the form of extracellular matrix. The body structure is treated to remove cellular membranes, nucleic acids, lipids and cytoplasmic components. Such structures are implanted internally in the body or externally on the body in a variety of medical uses.

15 Claims, No Drawings

BODY IMPLANTS OF EXTRACELLULAR MATRIX AND MEANS AND METHODS OF MAKING AND USING SUCH IMPLANTS

The invention described herein was made in the course of work under a grant or award from the National Institute of Health.

RELATED APPLICATION

This application is a continuation-in-part of U.S. patent application Ser. No. 503,203, filed June 10, 1983.

BACKGROUND OF THE INVENTION

A large variety of body implants are known for medical uses such as substitute vascular prostheses, skin dressings and coverings, and for other purposes. The implant materials can be synthetic or body tissues from the same species or other species as the species to be implanted. When body tissues and structures are to be implanted, they may be used fresh from the donor but in many cases, it is preferred to have some means of preserving the implant tissue for later use.

Umbilical cords have been suggested for use as vascular grafts after storage in buffer and fixing with glutaraldehyde. Bovine carotids have been treated with ficin to form collagenous materials for later implantation. Others have extracted lipids from cross-linked body materials to be implanted. U.S. Pat. No. 4,323,358 does disclose the use of a sodium dodecyl sulfate treatment of a body implant material which has first been treated with glutaraldehyde. The treatment is carried out only after cross-linking and inhibits mineralization on implantation. None of these known procedures has resulted in a totally acceptable and reproduceable vascular graft suitable for acceptance by all although each has certain advantages. The use of biomatrix as a supplement and aid in tissue culture outside of the body has been suggested by many including U.S. Pat. No. 4,352,887. Biomatrix fibers are used for tissue culture after treatment of body structures with a series of steps including detergent treatment to remove cell membranes, nucleic acids, lipids and cytoplasmic components while leaving a material high in collagens. The treatment of whole body structures with detergent steps of various sorts has been suggested to obtain extracellular matrix suitable for scientific study. Papers on this subject include the following: K. Brendel and E. Meezan, "Vascular Basement Membranes: Preparation and Properties of Material Isolated with the Use of Detergents", The Cerebral Microvasculature, 1980, pp. 89-103; E. C. Carlson, K. Brendel, J. T. Hjelle and E. Meezan, "Ultrastructural and Biochemical Analyses of Isolated Basement Membranes from Kidney Glomeruli and Tubules and Brain and Retinal Microvessels", Journal of Ultrastructure Research, 62, 26-53 (1978); R. C. Duhamel, E. Meezan, K. Brendel, "Morphology of Bovine Cerebral and Retinal Microvascular Basement Membranes and Electrophoretic Characterization of Differential Extracts", Bibliotheca Anatomica, No. 20, pp. 134-137; E. Meezan, K. Brendel, J. T. Hjelle and E. C. Carlson, "A Versatile Method for the Isolation of Ultrastructurally and Chemically Pure Basement Membranes Without Sonication", Biology and Chemistry of Basement Membranes 1978, pp. 17-30; E. Meezan, R. B. Nagle, P. Johnson, C. Wagner, R. White and K. Brendel, "Structural and Functional Properties of Acellular, Histoarchitecturally Intact Basement Membranes", Frontiers of Matrix Biology, vol. 7, pp. 101-119 (1979); E. Meezan, J. T. Hjelle and K. Brendel, "A Simple, Versatile, Nondisruptive Method for the Isolation of Morphologically and Chemically Pure Basement Membranes from Several Tissues", Life Sciences Vol. 17, pp. 1721-1732 (1975); K. Brendel, E. Meezan and R. B. Nagle, "The Acellular Perfused Kidney: A Model for Basement Membrane Permeability", Biology and Chemistry of Basement Membranes, pp. 177-193 (1978); R. Kuttan, R. D. Spall, R. C. Duhamel, I. G. Sipes, E. Meezan and K. Brendel, "Preparation and Composition of Alveolar Extracellular Matrix and Incorporated Basement Membrane", Lung (1981) 159:333-345; and R. C. Duhamel, E. Meezan and K. Brendel, "Selective Solubilization of Two Populations of Polypeptides from Bovine Retinal Basement Membranes, Exp. Eye Res (1983) 36, 257-267.

The prior art has not recognized the substantial advantages obtained by use of body implants which have been treated to form them into cell-free extracellular matrix high in collagens and suitable to provide body repair and compatibility in a wide range of specific living body locations having a wide range of functions.

SUMMARY OF THE INVENTION

It is an object of this invention to provide sterile body implants comprising body derived whole structures having as a major component collagens in the form of extracellular matrix from which has been removed cellular membranes, nucleic acids, lipids, and cytoplasmic components.

It is an object of this invention to provide novel body implants from living bodies which can replace and repair body structures and which is non-antigenic to the body.

Another object of this invention is to provide improved methods for treating body tissues to enable their reimplantation in the bodies of others to repair and replace selected body structures.

Still another object of this invention is to provide an improved method for forming extracellular matrix from structures taken from the body and to provide methods of using such matrix materials in the body.

The method of this invention broadly comprises forming a body implant from a body tissue which has been treated with a denaturing detergent to obtain the structure in extracellular matrix form.

In the preferred method of treating body tissue to remove cellular membranes, nucleic acids, lipids and cytoplasmic components and form extracellular matrix having as its major component collagens and making the body tissue suitable for use as a body implant, a first non-denaturing detergent is used to remove cytoplasmic cell membranes but not nuclear membranes while preventing degradation of extracellular matrix. A second strong denaturing detergent is then used to dissolve nuclear membranes after which both detergents are removed while maintaining the tissue in sterile form for use as a body implant. Preferably the first detergent is used with a protease inhibitor and may or may not have a DNase added. Thus, the first soaking of the body tissue removes cell membranes and disrupts lipids but also does not allow the proteases present in the cells to digest or destroy collagens present. The DNA can be partially solubilized and partially removed by either natural DNase or added DNase.

In a second step preferably after washing away the first detergent, a denaturing detergent is used to unfold proteins remaining and solubilize them and also remove nuclear membranes. The use of a first step soaking with the non-denaturing detergent permits partial hydrolysis and partial removal of DNA from the tissue material so that highly viscous DNA does not interfere with the action of the second detergent. The highly viscous DNA is modified prior to its complete removal in the second detergent step.

In subsequent steps, the detergent is removed preferably by extensive washing which can be for several hours or days at room temperature.

In a third step, the extracellular matrix formed can be sterilized as with ethylene oxide or irradiation as known and maintained sterile for subsequent use. The whole structures such as carotid arteries that have been treated in accordance with this invention can e lyophilized for subsequent implantation or maintained sterile in a liquid base under conventional conditions. In some cases, glutaraldehyde or other cross-linking treatments can be used as is known for tissue structures. Such cross-linking may be desired in certain implants.

It is a feature of this invention that the body implants can retain the biologically relevant histoarchitecture of the tissue which they are replacing or repairing. The body implants retain physical properties such as strength, resiliency, density, insolubility and permeability. The primary structure of the extracellular matrix in a physical form having biologically relevant spatial arrangements retained along with certain collagens and proteins which are important for regulated ingrowth of new cells. Grafts and other tissues can serve as suitable conduits for recellularization when reimplanted in a body and the recellularization occurs in a biologically relevant fashion to obtain an implant which retains many of the natural physical properties of graft or other tissues. When used in grafts, the implants do not show strong thrombogenic interactions with flowing blood except at extremely small diameters (less than 100 micrometers).

The body implants of this invention are of cell-free extracellular matrix which contains a significant portion of the original tissue mass retaining physical properties in regard to strength and elasticity and has components which are largely collagens but also comprise glycosaminoglycans and proteins closely associated with collagen such as the basement membrane complex, laminin and fibronectin. In the cell-free extracellular matrix of this invention which is formed from body tissues other than bone and particularly from blood vessels and ligaments, elastin is a major component along with collagens but usually in somewhat lower amounts than collagens. This varies with different tissue types and in certain tissue such as ligaments, resultant extracellular matrix thereof has more elastin than collagen. As used herein, extracellular matrix shall mean such material as described above in this paragraph formed by having been extracted with at least one detergent.

DESCRIPTION OF PREFERRED EMBODIMENTS

Natural body tissues from animals and man such as pig, cow, dog, norse and the like can be used as starting materials to form the body implants of the present invention. Minimized antigenic properties can often be obtained when the same species is used for the starting material as to be used for the implanting although as a practical matter, when dealing with implants for man, the species is often other mammals for derivation of the starting material. The starting tissues are preferably the same as the tissues where the materials are going to be implanted. For example, vascular valves can be replaced with vascular valve materials from another body which had been treated according to this invention. Arteries and veins can be used for replacing arteries and veins and the like. Bones and teeth can be used for replacing bones and teeth and skin for replacing skin. However, in many cases, as for example in skin grafts, various high strength tissue materials can be used as the starting material such as pericardium and dura matter which can be used as a skin implant to dress burn wounds and the like.

In all cases, the body implants are formed from body tissues obtained upon autopsy or sacrifice without prior fixation with preservatives, tanning agents or deleterious enzyme treatments. Preferably the tissue to be treated is obtained in a fresh state and treated immediately in accordance with the methods of this invention.

Basically detergents are used to remove cellular components from tissues not previously altered by treatment with enzymes, fixatives, protein denaturants, cross-linking agents, sterilants and the like. After treatment of the tissue with detergents, additional steps are taken to remove detergent residues, obtain a sterilized implant which can be maintained sterile and in some cases adding improved physical properties to the implant such as cross-linking for increased strength in certain tissue types.

The body implants fall into four general types which includes vascular prostheses such as carotid artery replacement, and general vein and artery replacement in the body, heart valves and patches, burn dressings and coverings, and tooth and bone implants. Preferred body implants include vascular prostheses from explanted human arteries and human umbilical cords for implantation in humans; arteries and veins from primates, dogs and other animals for implantation in humans; venous prostheses complete with valves from explanted human veins for implantation in humans or from animal veins for implantation in humans. Heart valves can be taken from human autopsy or donor tissue for implantation in humans or the source can be slaughterhouse animal tissue for implantation in humans. Pericardium, pericardial sac, dura mater, omentum, mesentery and conjunctiva from human autopsy donor tissue, or from slaughterhouse animals can be used in surgical reconstruction. Bone pieces, cartilage and ligaments from human autopsy or animal tissue can be used in surgical reconstruction. Tooth implants can be obtained and treated and reimplanted in human teeth sockets to provide prosthetic devices. Skin or gut of animal origin can be used for burn wound dressing. Freshly explanted tissues rich in extracellular matrix such as arteries, veins, umbilical cords, skin, bone, teeth, cartilage, intestinal wall, ligaments, and the like are preferred for use. Other body implants can be formed in accordance with the present invention. The original body tissues and structures used are such that they can be treated with detergents of this invention to obtain materials which have the required non-immunogenicity, non-thrombogenicity and favorable surface characteristics for ordered recellularization. Muscle tissues are not preferred for use.

According to the preferred detergent processing method, excised living tissue is preferably soaked with a solution of a non-denaturing detergent such as an aqueous solution of Triton X-100, a trademarked product of Rohm and Haas Company of Philadelphia, Pa. such as a 1% solution with from 0.5 to 20% being acceptable. The purpose of the first soaking detergent is to remove the cellular membrane and proteins by disrupting lipids. The solution is preferably changed at least two or three times and preferably more until clear washings are obtained. This first detergent step is preferably carried out at room temperature with the exchange of soaking detergent preferably changed every hour for the first three to five hours. The temperature can vary greatly and can be from 1° C. to 40° C. with exposures of from a few hours to several days. The pH is preferably held between 6 and 8 but can vary between 4 and 9. In some cases, protease inhibitors are used to prevent degradation of the extracellular matrix and preferably prevent naturally occurring proteases from attacking collagens. In some cases, natural protease inhibitors provide sufficient protection.

The protease inhibitors can include collagenase inhibitors such as ethylenediaminetetraacetic acid in concentrations of from 1 to 25 millimolar, sulfhydryl protease inhibitors such as NEM in concentrations of from 1 to 25 millimolar and serine protease inhibitors such as PMSF in concentrations of from 0.2 to 1 millimolar. The temperature is maintained above the Kraft point of the detergent or temperature at which there is no phase separation. Preferably 1-24 hour periods are used at temperatures of from 10° to 30° C.

In some cases DNase can be used along with the first detergent. This allows the DNA present to be solubilized and partially removed by either natural DNase or the added DNase. Even if the DNase is not added, DNA is removed and solubilized. The DNase if added can pass through the nuclear membrane and enter the nucleus. Any DNA remaining after the first detergent treatment step is in a non-viscous form which does not act to restrict diffusion of detergent and proteins remaining in the treated material during a second detergent step.

After the first detergent step, distilled water washing is preferably carried out in order to remove traces of detergent. In some cases this can be omitted although it is preferred to prevent possible blocking action to the second detergent used.

A second detergent step is used with soaking in a denaturing detergent which can be used above its critical micellar concentration. Such soaking can be used for times of from 1 to 7 days or longer with 3 days being preferred for most small body tissue structures treated, such as for 10 to 15 centimeter long arteries. Temperatures of from 4° to 30° C. can be used with detergent concentrations often approaching 1%. Preferably 10° to 30° C. is used for soaking times of 3 days.

The second detergent step unfolds protein that was not cross-linked and solubilizes such proteins removing them along with the nuclear membrane.

The second denaturing detergent is then washed out with the use of distilled water. Often saline solutions can be used for rinsing and washing to maintain the physiological conditions of the tissue under body conditions. Preferably alcohol such as 70% ethanol is added as a washing solution to act as a bacteriacide and aid in removal of detergent traces.

After washing, the body tissues treated in accordance with this invention can be stored in 70% alcohol, freeze-dried, fixed with glutaraldehyde, further sterilized with ethylene oxide, gas sterilization or gamma irradiation all as known in the art for treating body tissue to be reimplanted in the body.

It should be understood that the detergents used can be many and various conventional additives can be used such as bacteriacide materials in the first and second detergent steps.

In some cases, only the second detergent step need be used with sufficient material removed from the body tissue being treated to enable it to act in the form of extracellular matrix for use as a body implant. In other cases, only the first detergent step need be carried out although it is much preferred to use a denaturing detergent preferably in a second step. In some cases mild denaturing detergents may be used in a single step along with a non-denaturing detergent as for example the use of deoxycholate in conjunction with the Triton X-100.

Among the many detergents that can be used for the non-denaturing detergent are other polyoxyethylene ethers with Triton X-100 being one trademarked product which is a polyoxyethylene ether. Triton X-114 can be used. NP-40 an octylphenolethylene oxide produced by Shell Chemical Company can also be used as can polyoxyethylene sorbitans of the Tween series such as Tween 20, Tween 40 and Tween 60. Brij 35, a polyoxyethylene ether produced by ICI Americas Incorporated of Wilmington, Del. can also be used. In general any detergent which is non-denaturing, disrupts cytoplasmic or cell membranes but not the nuclear membrane can be used in the first step. It is important that the nuclear membrane remains physically intact during the first step while permitting activation of endogenous nucleases (DNase) or the entry of exogenous nuclease. If the detergent does not allow the nuclear DNA to be hydrolyzed before lysis of the nuclear membrane, the DNA is released. DNA is viscous and can entrap proteins and make subsequent extraction steps more difficult but not impossible.

The second detergent which is capable of dissolving the nuclear envelope and nuclear contents is preferably sodium dodecyl sulfate or a detergent formed with an aqueous solution of a water soluble salt of a sulfated higher aliphatic alcohol or sulfonated alkane or sulfonated alkylarene containing from 7 to 22 carbon atoms. The alkyl unit may be straight chain or branched and preferably alkyl sulfates including the water soluble salts of lauryl sulfate, myristyl sulfate, cetyl sulfate, steryl sulfate and oleyl sulfate are used. Mixtures of two or more other detergents in any of the detergent steps can be used if desired. Suitable salts include the sodium, potassium, lithium and ammonium salts of C7-22 alkyl sulfate or sulfonates or alkylarene sulfonates and amine salts such as triethylamine-lauryl sulfate. Concentration of the detergent is preferably in the range of from 0.5 to 10%. By the term "denaturing detergents" as used in this application is included those detergents that denature or unfold proteins or dissolve nuclear membranes. Preferably these denaturing detergents are anionic detergents. Other detergents useful as denaturing detergents include deoxycholate at concentrations of from 0.5 to 4%. Because of low insolubility at low pH, deoxycholate solutions should be buffered preferably at pH 8 but always within the range of about pH 7 to about pH 9.

Bacteriostatic agents are preferably used throughout or at least in the first detergent step and can be removed with water. Sodium azide in concentrations of from 0.01 to 0.5% is preferred. Mercurochrome and antibiotics can also be used. Alternatively, all solutions can be sterilized by heat and the entire procedure performed under sterile conditions.

Two strategies are employed to minimize proteolytic damage of the extracellular matrix. In one method, the released proteases are rapidly diluted and washed away by using large volumes of solution and frequent exchanges of the Triton solution or first detergent. In a second strategy, one or more protease inhibitors are included with the first detergent. The several classes of proteases as discussed above can be inhibited by added inhibitors recited below:

(a) The serine-dependent proteases are inhibited by activated organic phosphates and thiophosphates, such as phenylmethylsulfonylfluoride (PMSF) or diisopropyl phosphofluoridate.

(b) The sulfhydryl-dependent proteases are inhibited by inhibitors of sulfhydryl groups such as N-ethylmaleimide (NEM), glycidol, ethacrinic acid, and the like.

(c) The divalent-cation-dependent proteases are inhibited by chelating agents such as ethylenediame tetracetate (EDTA), ethylene glycol-bis($\beta$-amino-ethyl ether) N,N,N',N'-tetraacetic acid.

(d) The acid proteases are inhibited at neutral pH.

It is found that use of 0.2 millimolar PMSF alone is satisfactory when treating dog carotid arteries but when more active proteases are present in the tissue being treated, it is preferred to employ a plurality of inhibitors as for example 0.2 millimolar PMSF, 1-25 millimolar NEM, 1-25 millimolar EDTA in a buffer at pH 6.5 to 8.5.

Once the body tissue structures of this invention have been treated with detergents as described, they can be implanted in the body by conventional techniques. Thus, vascular grafts can be made to replace carotid and other arteries and veins in the human body. Such vascular grafts of dog and other tubular materials have been found to be patent over long time periods and provide for desirable characteristics over long time periods.

The above and other objects, advantages and features of the present invention will be better understood from the following descriptions of theoretical and actual examples of methods of producing and using extracellular matrix body implants of the present invention.

EXAMPLE 1

Human carotid arteries, spermatic arteries and other arteries which have no branches for at least 20 cm are resected using sterile techniques upon autopsy. All arteries are flushed upon resection with cold 0.9% saline to remove blood and clots. Two washed vessels are then transferred to a sterile covered pan containing 200 ml 1% Triton X-100 solution. This and all subsequent solutions are sterilized by autoclaving. The Triton X-100 solution also contains 0.02% sodium azide, 1 mM disodiumethylene diaminotetraacetate (EDTA) and 1 mM N-ethylmaleimide (NEM). The vascular explants are agitated in this solution by shaking in a gyratory shaker at room temperature. The solution is replaced every hour for three hours. At this time, the solution is replaced with a 1% Triton X-100 solution containing 0.5 mM phenylmethylsulfonylfluoride in which the vascular explants are agitated for 1 hour. After this treatment, the vessels are transferred to 1% Triton X-100 containing 0.02% sodium azide and incubated for the next four days with daily exchanges of the extractant. After this period of time, the extracellular vascular matrix is washed extensively with many changes of sterilized double-distilled water, then several 24 hour exposures to 70% ethanol in order to be finally stored in 70% ethanol until preparation for implantation. Storage in 70% ethanol is possible for extended periods of time. Before implantation, the vascular graft is washed in 0.9% sterile saline with several exchanges and then soaked in a small amount of heparinized saline. Implantation proceeds via standard procedures in vascular surgery. Instead of exposure to four days of Triton X-100, one cay Triton X-100 followed by three days 1% sodium dodecylsulfate may be substituted.

Differences in these treatments are not obvious as measured by histology but might be important in recellularization and turnover of the implanted cellular, vascular, extracellular matrix.

EXAMPLE 2

Human umbilical cords are frozen after resection from the placenta immediately upon delivery. Damaged or otherwise unsuitable cords are discarded. Those cords deemed suitable for further treatment are cannulated unilaterally at the umbilical vein observing sterile procedures and are then attached to an apparatus which permits perfusion of the tissue in both recirculatory modes and at the same time bathes the tissue in the perfusate. A sterile solution of 1% Triton X-100 is then slowly perfused through the cannulated cords for several hours. After discarding the first perfusate, the solution is replaced by sterile 1% Triton X-100 containing 0.02% sodium azide 1 mM disodiumethylenediaminotetraacetate, 1 mM N. ethylmaleimide and 0.5 mM phenylmethylsulfonylfluoride in phosphate buffered physiological saline at pH 7.5 which is recirculated through the cords for a period of 24 hours. This solution is exchanged with fresh identical solution and perfusion continued for another day. On the third day, the perfusate is replaced by a solution containing 1% sodiumdodecylsulfate, 0.02% sodium azide and adjusted to 320 milliosmolar with phosphate buffered saline. This solution is perfused through the cords for the next three days with daily exchanges. At the end of the fifth 24 hour period the cords are washed with filter sterilized reverse osmosis water until all obvious evidence for the presence of detergents (foaming) is absent. This procedure is done in a nonrecirculatory perfusion mode. The cords are then returned to phosphate buffered physiological saline at pH 7.5 and perfused in recirculatory fashion with an activated charcoal filter followed by a small particle filter in line to remove the last traces of detergents. This procedure is followed by extension fixation inside a stainless steel mesh outer mandril at pressures ranging from 0.1 to 0.5 bar with a solution containing 1% glutaraldehyde and 1% sodium chloride. This extension fixation step is carried out at room temperature and for up to 24 hours. Fixation is followed by washing with filtered reverse osmosis water and capping, a procedure in which the isolated human umbilical cord extracellular matrix is exposed to solutions of aminoacids or proteins in water with the result of binding these to the exposed glutaraldehyde sites achieving both surface modification and covering of reactive sites simultaneously. From this capping bath the materials are returned to a wash bath and then into the final storage solution. Upon preparation for surgery the human umbilical cord extracellular matrix is removed from the storage solution and washed and flushed with sterile saline and then heparinized sterile saline. The entire procedure is done under sterile conditions, all equipment is autoclaved, all solutions either autoclaved or filter sterilized.

EXAMPLE 3

Human heart valves are resected carefully and using sterile technique upon autopsy and stripped of all adhering tissue. The valves are then floated in the solutions indicated under Example 1 in the same sequence and for similar times. Mechanical scraping and brushing removes remains of muscular tissue present at the periphery. The valve is then sown into a suitable retainer ring washed and sterilized. All work is done in hoods with filter and UV sterilized air laminar air flows.

EXAMPLE 4

Not only tubular structures such as vessels and complex valves can be treated in the procedure to result in the corresponding acellular matrix materials, but also membranous tissue sheets such as pericardium, omentum, mesentery, conjunctiva, etc. obtained upon autopsy from humans, in the slaughterhouse—from cows, pigs, sheeps, etc., or in the laboratory—from larger laboratory animals, may be treated in essentially the same fashion. If and when layers of muscle tissue are adjacent to the connective tissue matrix, additional mechanical operations might become necessary such as splitting layers and scraping to remove muscle tissue remnants. Such operations may be done before, during or after the detergent extraction procedure is completed. The extraction procedure itself is similar to those described in Examples 1-3.

EXAMPLE 5

Small pieces of bone, thin sections of cartilage and ligaments are freed of all cells by the same procedure described in Example 1 and the resulting extracellular bone cartilage and ligament matrix materials are used in the surgical fusion of the vertebrae column reconstruction of bone and ligaments. In order to retain the inorganic components of bone intact during the procedure of this invention, the solutions employed are saturated with hydroxyapatite by passing through cartridges loaded with that material.

EXAMPLE 6

The reimplantation of human teeth is another application of the method of the present invention. Here, extracted or avulsed teeth are treated with a succession of solutions similar to the above-described procedures in Example 1. A small hole is drilled into the crown of the tooth and detergent solutions sucked through this hole via the root canals from an outside bath in which the tooth is suspended. To spare the mineral material of the tooth, hydroxyl or fluoro apatite is placed into contact with the extractants. Extensive clean-up procedures remove all traces of the extractants. Finally, sterilization precedes reimplantation. A kit can be developed to make it possible to perform this procedure in a dental laboratory.

EXAMPLE 7

If skin is obtained from pigs in the slaughterhouse, it is important that the animal is not hosed off with hot water in excess of 40° C. The whole skin is obtained as soon after death as possible and brought to the laboratory, cut into 6-inch wide strips and mechanically cleaned with a 1% Triton X-100 solution. Hair is then removed with a razor and the strips soaked in 1% sodium dodecylsulfate solution (approximately 10 times the volume of the strips). The sodium dodecylsulfate solution is exchanged every 48 hours for a total of 144 hours, and at that time the strips are scraped on both sides which removes the keratin layers together with any pigment which might be present as well as the remnants of subcutaneous fat tissue. At this time the strips of skin are completely white but have retained their former properties in regard to physical strength, dimensions and general appearance. The strips are now split with a dermatome and the upper layer approximately 1000 $\mu$m thick washed extensively with filter sterilized reverse osmosis water. The washed strips are then immersed into 70% ethanol for 144 hours and the alcohol exchanged every 48 hours. At the end of this treatment, the strips are washed with sterile reverse osmosis water again and then immersed into a bath of 1% glutaraldehyde for 24 hours. Excess glutaraldehyde is washed off with sterile RO water using scrupulously sterile conditions from then on. The strips are then lyophilized in a stretched out flat position and packed into ethylenoxide sterilized plastic bags. Alternatively, the strips of pig skin extracellular matrix may also be lyophilized before the glutaraldehyde step and lyophilized at this stage, a treatment which is followed by ethylene oxide sterilization (<40° C.) and packaging into sterile plastic bags.

The lyophilized pig skin extracellular matrix when kept dry, dark and cool, has an indefinite shelf life. Reconstruction of the material is done by soaking in sterile saline containing antibiotics. This material may then be used as a temporary dressing for large-area, third-degree burn wounds.

EXAMPLE 8

Burn wound dressings can be produced from sections of small intestine freshly obtained from slaughterhouse animals, washed and slit lengthwise, then scraped on the inside to remove most of the mucosal tissue. These prewashed intestinal strips are then immersed into sodiumdodecylsulfate solution in a regimen similar to the one described under Example 7. At the end of the detergent exposure period, the strips are scraped on both sides to remove remnants of adhering smooth muscle layers. The resulting gut extracellular matrix material is then immersed into alcohol as described in Example 7 and washed extensively with sterile RO water. This treatment is followed by immersion into a 1% glutaraldehyde solution containing 30-50% ethanol. This solution is a combined fixative sterilant and storage solution.

For reconstitution, the gut extracellular matrix strips are soaked in sterile saline which is exchanged several times. Finally, the strips are soaked in an antibiotic saline solution and applied moist to large-area, third-degree burns.

EXAMPLE 9

Accelular vascular matrix (AVM) is prepared as follows:

Adult greyhounds were used as donors for native carotid artery. The animals were premedicated with Xylazine (1.0 mg/lb) and anesthetized with intravenous sodium pentobarbitol (11.0 mg/lb). The animals were intubated and placed on a volume ventilator (Harvard pump). Both carotid arteries were mobilized and harvested using aseptic surgical technique through a single midline incision. Explanted carotids were unbranched and averaged 3-4 mm outside diameter and 12-15 cm in length. The arteries were rinsed in saline prior to detergent treatment. The arteries were incubated in 1% Triton X-100, 0.02% sodium azide, freshly-dissolved 2 mM phenylmethylsulfonylfluoride (PMSF), 5 mM MgCl₂ for 1 hour at room temperature. The arteries were transferred to fresh volumes of the same solution at hourly intervals for 3 hours. After Triton treatment, the arteries were incubated in 1% sodium dodecylsulfate (SDS) for 72 hours with daily exchanges. The resulting AVM was then extensively washed for 24 hours, first in distilled water and then in 70% ethanol in order to remove all traces of remaining detergent. AVM to be crosslinked were rehydrated in distilled water prior to further treatment. Detergent treatment and the water and ethanol washes were performed by swirling on a gyratory shaker. Arteries were processed in lots of 8–12 in 300 ml of solution. These arteries are described as "Extracted no crosslinking" in Table 1.

Some of the extracted dog carotid arteries above are immersed in a 1% solution of 1-ethyl-3-(3-dimethylaminopropyl)-carbodiimide HCl for the period of 60 minutes at 25° C. and then washed with water before they were either exposed to a 5% glycine solution or a 5% solution of partially N-desulfated heparin. These treatments were followed by extensive washing in distilled water and then saline, followed by water. After this treatment, the chemically modified acellular vascular matrix materials are stored in 70% ethanol until preimplantation washing in distilled water and heparinized saline. The carbodiimide treated arteries are described as "Extracted Crosslinking" in Table 1 and Group III is the heparinized treated batch of arteries.

SURGICAL PROCEDURES

Graft Collection

Adult greyhounds were anesthetized with an intravenous injection of Sodium Pentobarbital, followed by euthanasia with T-61 euthanizing agent.

A ventral midline incision was made on the neck to allow bilateral dissection of right and left common carotid arteries from the thoracic region to the thyroid artery bifurcation. The carotids were excised and flushed thoroughly with a heparinized normal saline solution.

Each explant specimen was individually contained in heparinized saline and labeled prior to refrigeration. All explants were transported on ice as soon as possible for further processing.

Average length of grafts used ranged from 10–15 cm, which were later dissected to approximately 5 cm pieces.

Surgical Implantation

Adult male mongrel dogs weighing 20–40 Kg were given 300 mg aspirin each day for three days preceding surgery, and were starved 24 hours prior to their scheduled surgery; ketamine HCl (100 mg) was administered intramuscularly as a preanesthetic. Anesthesia was effected with an intravenous injection of sodium pentobarbital (20 mg/Kg body weight). An intravenous drip unit was placed using lactated ringers solution with 5% dextrose as fluid replacement during surgery. Normally each dog received 500–1000 ml during the course of surgery and post operatively. An endotracheal tube was placed and connected to a respirator. The neck region was shaved and prepared for sterile surgical procedure with five minutes of scrub and betadine solution application. Sterile drapes were placed and the remaining equipment was set up. Using standard sterile technique, a ventral midline incision was made in the neck to expose the right common carotid (RCC). Following a short length dissection of the RCC, topical application of 2% Lidocaine HCl was performed before blood flow measurements were recorded using Stratham-Gould flow probes and flow meter SP 2204. Dissection of the RCC was expanded to roughly 15–20 cm proximal to the thyroid artery bifurcation. Temporary aneurysm clips were applied proximally and distally to the area in which the graft was to be positioned. The RCC was then cut cleanly with a sharp iris scissor between the clips and the artery was flushed with heparinized normal saline.

Using a Zeiss operating microscope graft and carotid ends were trimmed and fitted for interpositional end-to-end placement. Graft length was approximately 5 cm. Using standard microvascular technique, end-to-end anastomasis was performed using a 135 micron needle on a 9-0 monofilament nylon. Sixteen interrupted sutures were placed for each anastomosis. Back flow-reperfusion techniques were applied for removal of air and the final reperfusion of the host and graft artery. Following topical application of 2% lidocaine HCl another blood flow measurement was recorded ten minutes post graft reperfusion. Graft length was measured post reperfusion for comparisons. Bacitracin solution was applied liberally in and around the wound prior to closure with absorbable polyglycolic acid suture materials. Dogs received an antibiotic regimen of 600,000 units penicillin G procaine, 0.75 gram dihydrostreptomycin sulfate daily for five days post operatively, and 300 mg aspirin daily for five days post-operatively, and 300 mg aspirin daily for 30 days post-operatively.

Graft Harvest

Three months (90 days) following the initial surgery, each dog was starved for 24 hours prior to graft harvest.

Following ketamine HCl preanesthetic and sodium pentobarbital anesthesia, the old midline incision was reopened to allow bilateral dissection of the RCC and LCC. Short length dissection of each carotid was performed at a far proximal region to determine graft patency and to record blood flow measurements of the RCC (graft) and LCC (control) after topical lidocaine applications. With great care not to disturb the graft, the entire length of the RCC including the graft was dissected to facilitate the perfusion-fixation procedure and as insurance against blood back flow through small aterioles and adventitial vessels during perfusion-fixation.

Allowing 3–5 cm from each end of the graft, a clamp is applied to the host carotid proximal and adjacent to the thyroid bifurcation. The RCC is then ligated as far proximally toward the thoracic region as possible. The arterial catheter is inserted on the graft side of the ligature and tightly tied in place with another ligature. The catheter is connected directly to a three-way stopcock with a 60 cc syringe on the end. The syringe and catheter is full of flush medium (heparinized normal saline) when inserted. As the distal clamp is released a constant even pressure is applied to the syringe and monitored with an in-line pressure gauge to a level of 300 mm Hg. As the first syringe is emptied, on signal the distal clamp is simultaneously closed with the stopcock, trapping internal pressure. The second flush syringe is connected to the stopcock and on signal the distal clamp and stopcock are reopened while applied syringe pressure maintains the pressure. This sequence is repeated until four 60 cc syringes of flush have been delivered. The fifth syringe contains Karnovsky's fixative and is perfused exactly as the previous four flushes except that as the syringe is emptied another clamp is applied 3-5 cm proximal to the graft in addition to the distal clamp. The fixative is trapped at pressure in the segment and is kept undisturbed while bathing the outside of the segment in Karnovsky's for 15-20 minutes. The dog is euthanized immediately following the final perfusion of fixative.

After the initial fixation period, the segment is excised from the dog with clamps still intact and placed in fixative bath for an hour before sectioning or storing in cold fixative for later sectioning. Proximal or distal ends are flagged to maintain proper orientation when sectioning and later scanning electron microscopy.

Graft Specimen Sectioning

The intact graft with host artery ends is laid out on gauze soaked with Karnovsky's fixative. Starting at the proximal end, the specimen is transsected with a new double-edged razor blade held firmly in a large hemostat about 15 mm proximal to the proximal anastomosis. This transsection cutting is continued along the specimen allowing 5-8 mm between cuts. Care is taken to first map out where each cut is made to insure that each anastomosis will exhibit sufficient areas of both host and graft. Each section is cut through on a wall longitudinally exposing the full luminal surface. Two additional longitudinal cuts are made through the exposed lumen dividing each section into three equal specimens of exposed luminal surface. These pieces are placed such that the proximal ends are resting on the bottom of a culture tube of small bore. A loosely packed gauze piece is inserted over the specimens to secure their orientation in the tube. The tube is filled with fresh, clean Karnovsky's fixative and the air is removed from the bottom tube area. The tubes are labeled then stored in refrigeration until further preparation for scanning electron microscopy.

TABLE 1

| DOG I.D. & (Graft Type-Group) | SEX | BLOOD FLOW Pre Rcc CONTROL | BLOOD FLOW P OP 10' Rcc | BLOOD FLOW SACRIFICE Lcc-CONTROL | BLOOD FLOW SACRIFICE Rcc Graft |
|---|---|---|---|---|---|
| Group I. Extracted No Crosslinking | | | | | |
| Dog | A | 265 | 240 | 165 | 122 |
| Dog | B | 355 | 300 | 155 | 160 |
| Dog | C | 290 | 248 | 390 | 203 |
| Dog | D | 157 | 245 | 150 | 140 |
| Dog | E | 270 | 245 | 300 | ±10 |
| Group II Extracted Crosslinking | | | | | |
| Dog | F | 190 | 320 | 215 | 160 |
| Dog | G | 215 | 205 | 150 | 60 |
| Dog | H | 178 | 250 | 175 | 155 |
| Dog | I | 116 | 145 | 125 | 96 |
| Dog | J | 305 | 340 | 280 | 290 |
| Group III Extracted Crosslinking & Heparin | | | | | |
| Dog | K | 205 | 205 | 185 | 140 |
| Dog | L | 112 | 160 | — | — |
| Dog | M | 215 | 215 | — | — |
| Dog | N | 180 | 212 | 178 | 146 |
| Dog | O | 295 | 300 | 170 | 158 |
| Mean Values | (X̄) | 223.2 | 242 | 202.9 | 140.8 |
| St. Deviat. | (S) | 71.4 | 55.5 | 75.7 | 68.4 |
| No. # Data: | (N) | 15 | 15 | 13 | 13 |

| DOG I.D. & (Graft Type-Group) | SEX | GENERAL HEALTH at SACRIFICE | GRAFT PATENCY at SACRIFICE | GRAFT LENGTH Pre. O.P. | GRAFT LENGTH P OP. | GRAFT LENGTH at SACRIFICE |
|---|---|---|---|---|---|---|
| Group I. Extracted No Crosslinking | | | | | | |
| Dog | A | Excellent | Patent | 5.0 cm | 7.0 cm | 7.0 cm |
| Dog | B | Excellent | Patent | 4.3 cm | 6.0 cm | 6.0 cm |
| Dog | C | Excellent | Patent | 4.5 cm | 6.8 cm | 6.5 cm |
| Dog | D | Excellent | Patent | 4.5 cm | 6.5 cm | 6.5 cm |
| Dog | E | Excellent | 95% Occluded | 4.4 cm | 6.5 cm | 6.3 cm |
| Group II Extracted Crosslinking | | Patency: | 80% | x̄: 4.54 cm S: .27 cm | x̄: 6.6 cm S: .38 cm | x̄: 6.46 cm S: .36 cm |
| Dog | F | Excellent | Patent | 5 cm | 5 cm | 4.7 cm |
| Dog | G | Excellent | Patent | 4.3 cm | 4.4 cm | 4.3 cm |
| Dog | H | Excellent | Patent | 4.2 cm | 4.2 cm | 4.1 cm |
| Dog | I | Excellent | Patent | 4.8 cm | 4.8 cm | 4.8 cm |
| Dog | J | Excellent | Patent | 4.7 cm | 4.7 cm | 4.6 cm |
| Group III Extracted Crosslinking & Heparin | | Patency: | 100% | x̄: 4.6 cm S: .34 cm | x̄: 4.6 cm S: .32 cm | x̄: 4.5 cm S: .29 cm |
| Dog | K | Excellent | Patent | 4.7 cm | 4.7 cm | 4.6 cm |
| Dog | L | Good | Occluded | 4.0 cm | 4.2 cm | 4.0 cm |
| Dog | M | Poor | Occluded | 3.7 cm | 3.9 cm | 3.7 cm |

TABLE 1-continued
90 DAY CANINE - BIOGRAFT STUDY

| Dog | N | Excellent | Patent | 4.0 cm | 4.4 cm | 4.4 cm |
|---|---|---|---|---|---|---|
| Dog | O | Weak | Patent | 3.9 cm | 4.1 cm | 4.1 cm |
|  |  | Patency: | 60% | x̄: 4.0 cm | x̄: 4.3 cm | x̄: 4.16 cm |
|  |  |  |  | S: .38 cm | S: .30 cm | S: .35 cm |
| Mean Values | (X̄) |  |  | 4.4 cm | 5.1 cm | 5.0 cm |
| St. Deviat. | (S) |  |  | .4 cm | 1.09 cm | 1.09 cm |
| No. # Data: | (N) |  | 15 | 15 | 15 | 15 |

Example 9 is illustrative of the success of the detergent treated vascular grafts of this invention when used as body implants. However, it should be noted that not all dogs treated survived. When the tests are repeated, in some cases and during certain trials, only 68% of the grafts remained patent. It is believed that some of the failed grafts exhibited physical signs indicating that failure may have been due to mechanical problems associated with the suturing procedures which should be correctable by the use of microsurgical techniques. When grafts are implanted for carotid arteries, microsurgical techniques are preferred.

Example 9 can be repeated with the use of a modified detergent technique. For example, donor carotid arteries can be surgically removed from greyhound dogs, rinsed with saline and frozen. In a second step the arteries are thawed and incubated for 3 hours in 3% Triton X-100, 0.2% sodium azide, freshly dissolved 2 mM PMSF after which fresh solution is used for another 3 hours, followed by a third change of solution for overnight exposure at room temperature. Incubation is carried out with spleen DNase II (10 micrograms per ml) in 1% Triton X-100, 0.02% sodium azide, 2 mM PMSF, 5 mM $MgCl_2$, 20 mM phosphate buffer (pH 6.0) for 3 hours at room temperature. Incubation is then carried out at 4% deoxycholate overnight at room temperature. The material is then washed with 1% sodium bicarbonate followed by 50% ethanol to remove the deoxycholate. Rehydration is carried out in distilled water prior to surface or cross-link modification if desired.

Cross-linking is carried out with exposure to 1% glutaraldehyde at neutral pH for 24 hours at room temperature after which the grafts are washed several times with distilled water. Residual aldehydes can be blocked by reduction with 200 mg sodium borohydride in 20 ml borate buffer pH 9 for 1 hour at room temperature followed by washing with distilled water. The modified cross-linked prosthesis can be stored in 70% ethanol until required for surgical use.

Partially N-desulfated heparin can be used by washing the grafts with 0.1 N acetic acid in order to protonate all carboxylic groups followed by rinsing with distilled water. Five hundred mg of N-desulfated heparin in 50 ml of distilled water for 1 hour at room temperature is exposed to the grafts followed by washing with distilled water. The modified grafts can be stored in 70% ethanol until required for surgical use. Grafts prepared in accordance with this procedure are found to be useful as biological implants in dogs as carotid artery replacements.

While specific examples of the present invention have been described, many variations are possible. It is important that the body implants of acellular matrix be detergent treated prior to implantation in a body so as to remove antigenic components yet still provide a preformed material which can act as a body structure.

Vascular grafts having lengths of 12 to 15 centimeters long are preferred with diameters of from 0.5 to 30 millimeters at the lumen, or smaller diameters, are preferred while the most preferred range is 0.5 to 4 millimeters in lumen. Such tubular structures conform to the histoarchitecture of the tubes which they replace when used as body implants. They allow regrowth of cells and provide high patencies in a large variety of circumstance. Similarly other body implants when formed as acellular matrix prior to implantation into the body can be highly useful to repair portions of the body including all body tubes, heart linings and layers, skin and the like as described.

Standard implanting surgical procedures can be used to insert the matrix structures in mammalian bodies.

What is claimed is:

1. A sterile body implant comprising a body derived structure having as its major component collagens and elastin in the form of extracellular matrix from which has been removed cellular membranes, nucleic acids, lipids and cytoplasmic components.

2. A body implant in accordance with claim 1 wherein said implant is sized and dimensioned to be compatible with the histoarchitecture of a body portion to which the implant is to be attached.

3. A sterile body implant in accordance with claim 1 wherein said implant is treated shortly after said body structure is removed from the body and prior to substantial chemical cross-linking or change thereof with detergents.

4. A method of treating body tissue to remove cellular membranes, nucleic acids, lipids and cytoplasmic components and form extracellular matrix having as one major component collagens and making said body tissue suitable for use as a body implant, said method comprising extracting said tissue with a first and second detergent while maintaining said tissue in a suitable size and form for implantation in the body, said second detergent being a strong anionic detergent and removing said detergents while maintaining said tissue in sterile form for use as a body implant, said anionic detergent being selected from the group consisting of a water soluble salt of a sulfated higher aliphatic alcohol, sulfonated alkane and sulfonated alkylarene containing from 7 to 22 carbon atoms in a branched or unbranched chain.

5. A method in accordance with the method of claim 9 wherein said anionic detergent is sodium dodecylsulfate.

6. A method of treating body tissue to remove cellular membranes, nucleic acids, lipids and cytoplasmic components and form extracellular matrix having as one major component collagens and making said body tissue suitable for use as a body implant, said method comprising extracting said tissue with a first an second detergent while maintaining said tissue in a suitable size and form for implantation in the body, said second detergent being a strong anionic detergent and removing said detergents while maintaining said tissue in sterile form for use as a body implant, said first detergent being admixed with a protease inhibitor.

7. A method of treating body tissue to remove cellular membranes, nucleic acids, lipids and cytoplasmic components and form extracellular matrix having as one major component collagens and making said body tissue suitable for use as a body implant, said method comprising extracting said tissue with a first and second detergent while maintaining said tissue in a suitable size and form for implantation in the body, said second detergent being a strong anionic detergent and removing said detergents while maintaining said tissue in sterile form for use as a body implant, said first detergent being admixed with a DNase.

8. A method of treating body tissue to remove cellular membranes, nucleic acids, lipids and cytoplasmic components and form extracellular matrix having as one major component collagens and making said body tissue suitable for use as a body implant, said method comprising extracting said tissue with a first and second detergent while maintaining said tissue in a suitable size and form for implantation in the body, said second detergent being a strong anionic detergent and removing said detergents while maintaining said tissue in sterile form for use as body implant, said body implant being a bone implant.

9. A method of treating body tissue to remove cellular membranes, nucleic acids, lipids and cytoplasmic components and form extracellular matrix having as one major component collagens and making said body tissue suitable for use as a body implant, said method comprising extracting said tissue with a first and second detergent while maintaining said tissue in a suitable size and form for implantation in the body, said second detergent being a storing anionic detergent and removing said detergents while maintaining said tissue in sterile form for use as a body implant, said body implant being a tooth implant.

10. A method of treating body tissue to remove cellular membranes, nucleic acids, lipids and cytoplasmic components and form extracellular matrix having as one major component collagens and making said body tissue suitable for use as a body implant, said method comprising extracting said tissue with a first and second detergent while maintaining said tissue in a suitable size and form for implantation in the body, said second detergent being a strong anionic detergent and removing said detergents while maintaining said tissue in sterile form for use as a body implant, said body implant being a skin implant.

11. A method of implanting in a living body a whole structure for repairing the body, said structure being in the form of extracellular matrix high in collagen from which has been removed nucleic acids, lipids and cytoplasmic components leaving as its major component collagens with said removal being carried out by the use of at least one detergent, said method comprising implanting said structure in a living body, said whole structure being a tooth.

12. A method of implanting in a living body a whole structure for repairing the body, said structure being in the form of extracellular matrix high in collagen from which has been removed nucleic acids, lipids and cytoplasmic components leaving as its major components collagens with said removal being carried out by the use of at least one detergent, said method comprising implanting said structure in a living body, said whole structure being an area of the skin.

13. In a method of forming a body implant from a body tissue the improvement comprising treating said body tissue prior to cross-linking or unwanted deterioration of said tissue with a first non-denaturing detergent and a second denaturing detergent and forming said body implant therefrom suitable for use in implanting in a living body, said detergents being used in sequence and a protease inhibitor being used along with said first detergent.

14. A method in accordance with the method of claim 13 wherein a DNase is admixed with said first detergent.

15. In a method of forming a body implant from a body tissue the improvement comprising treating said body tissue prior to cross-linking or unwanted deterioration of said tissue with a first non-denaturing detergent and a second denaturing detergent and forming said body implant therefrom suitable for use in implanting in a living body, said second detergent being a strongly anionic detergent which is selected from the group consisting of a water soluble salt of a sulfated higher aliphatic alcohol, sulfonated alkane and sulfonated alkylarene containing from 7 to 22 carbon atoms in a branched or unbranched chain.

* * * * *